United States Patent

Osorio

[11] Patent Number: 5,674,069
[45] Date of Patent: Oct. 7, 1997

[54] CUSTOMIZED DENTAL ABUTMENT

[76] Inventor: Julian Osorio, 60 Federal St., Boston, Mass. 02110

[21] Appl. No.: 372,323

[22] Filed: Jan. 13, 1995

[51] Int. Cl.$^6$ .................... A61C 13/12; A61C 13/225; A61C 5/10
[52] U.S. Cl. ............................................ 433/172; 433/223
[58] Field of Search ............................ 433/172, 173, 433/174, 175, 176, 223

[56] References Cited

U.S. PATENT DOCUMENTS

| | | | |
|---|---|---|---|
| 4,937,928 | 7/1990 | Van Der Zel | 433/223 X |
| 4,964,770 | 10/1990 | Steinbichler et al. | 433/223 |
| 5,104,318 | 4/1992 | Piche et al. | 433/173 X |
| 5,125,839 | 6/1992 | Ingber et al. | 433/173 X |
| 5,180,303 | 1/1993 | Hornburg et al. | 433/173 |
| 5,297,963 | 3/1994 | Daftary | 433/173 X |
| 5,320,462 | 6/1994 | Johansson et al. | 433/223 X |
| 5,417,568 | 5/1995 | Giglio | 433/173 |
| 5,447,435 | 9/1995 | Brodbeck | 433/172 X |
| 5,476,383 | 12/1995 | Beaty et al. | 433/173 X |
| 5,492,471 | 2/1996 | Singer | 433/173 X |
| 5,497,336 | 3/1996 | Andersson et al. | 364/474.03 |

Primary Examiner—Nicholas D. Lucchesi
Attorney, Agent, or Firm—Edwin H. Paul; Perkins, Smith & Cohen, LLP

[57] ABSTRACT

A tooth replacement including an implant (24), abutment (2), and crown, where the abutment is shaped to match the tooth being replaced in inclination, orientation and gingival emerging profile. A method is also claimed where measurements of the teeth adjacent to the implant are taken along with other relevant oral measurements. These measurements are input to a computer which generates data for guidance and control of the forming of an abutment, including at least the size, shape, inclination, and orientation of the abutment. The abutment shape corresponds to that of the tooth being replaced, but of a reduced size such that the crown attached to the abutment matches the tooth being replaced. Preferentially, the abutment is both the healing and the permanent abutment which saves time, money and aggravation. The abutment is made of anyone or combinations of several metals and materials benign to the body, as are known in the art.

3 Claims, 12 Drawing Sheets

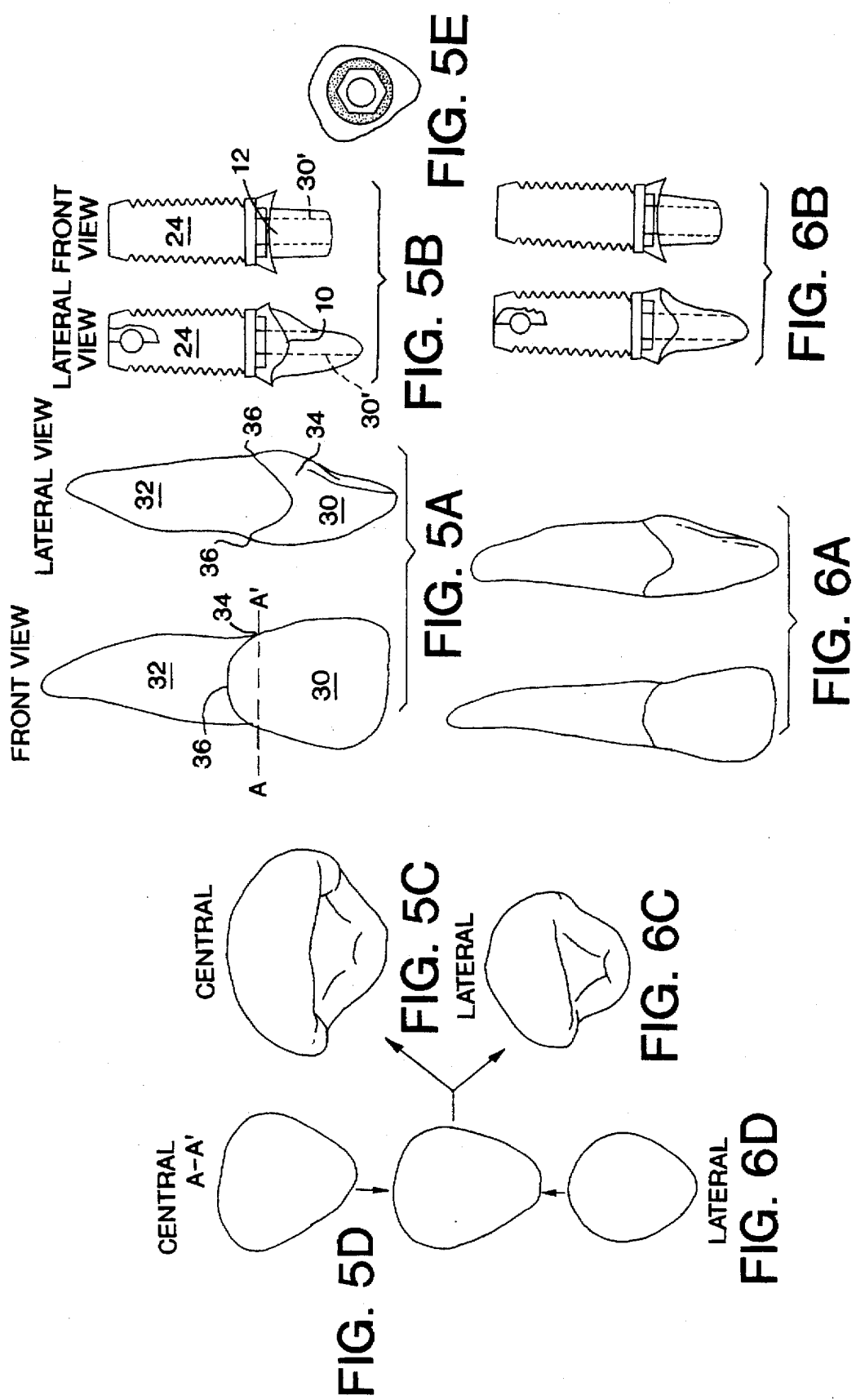

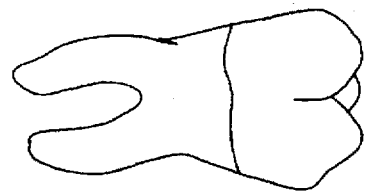
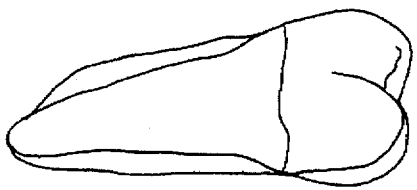
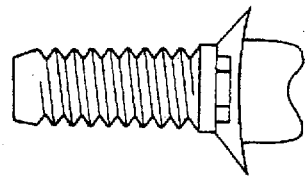
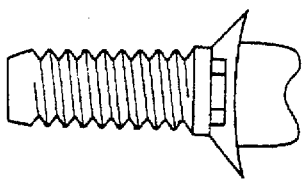
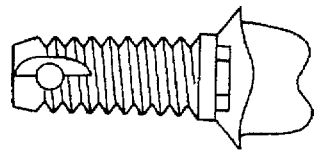
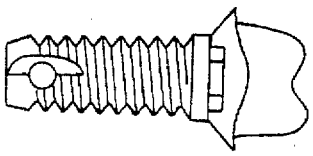
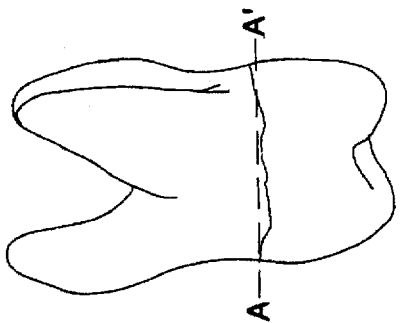
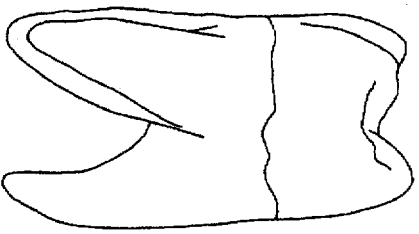
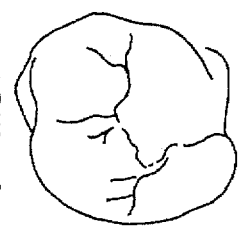
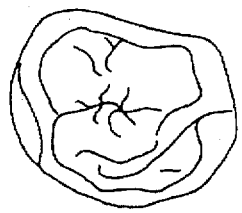
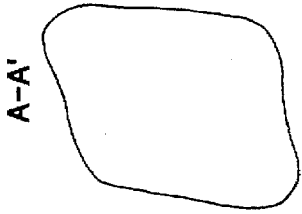
FIG. 8

TOOTH MEASUREMENTS

| | Cervico incisal length of crown (mm) 64 | Mesio-Distal diameter of crown (mm) 66 | Mesio-Distal diameter of crown at cervix (mm) 68 | Bucco-lingual diameter of crown (mm) 70 | Bucco-lingual diameter of crown at cervix (mm) 72 | Curvature of cervical line-Mesial (mm) 74 | Curvature of cervical line-Distal (mm) 76 |
|---|---|---|---|---|---|---|---|
| MAXILLAR | | | | | | | |
| CENTRAL INCISOR | 10.5 | 8.5 | 7.0 | 7.0 | 6.0 | 3.5 | 2.5 |
| LATERAL INCISOR | 9 | 6.5 | 5.0 | 6.0 | 5.0 | 3.0 | 2.0 |
| CANINE | 10 | 7.5 | 5.5 | 8.0 | 7.0 | 2.5 | 1.5 |
| FIRST PREMOLAR | 8.5 | 7.0 | 5.0 | 9.0 | 8.0 | 1.0 | 0.0 |
| SECOND PREMOLAR | 8.5 | 7.0 | 5.0 | 9.0 | 8.0 | 1.0 | 0.0 |
| FIRST MOLAR | 7.5 | 10.0 | 8.0 | 11.0 | 10.0 | 1.0 | 0.0 |
| SECOND MOLAR | 7 | 9.0 | 7.0 | 11.0 | 10.0 | 1.0 | 0.0 |
| THIRD MOLAR | 6.5 | 8.5 | 6.5 | 10.0 | 9.5 | 1.0 | 0.0 |
| MANDIBULAR | | | | | | | |
| CENTRAL | 9 | 5.0 | 3.5 | 6.0 | 5.3 | 3.0 | 2.0 |
| LATERAL | 9.5 | 5.5 | 4.0 | 6.5 | 5.8 | 3.0 | 2.0 |
| CANINE | 11 | 7.0 | 5.5 | 7.5 | 7.0 | 2.5 | 1.0 |
| FIRST | 8.5 | 7.0 | 5.0 | 7.5 | 6.5 | 1.0 | 0.0 |
| SECOND | 8 | 7.0 | 5.0 | 8.0 | 7.0 | 1.0 | 0.0 |
| FIRST MOLAR | 7.5 | 8.5 | 6.5 | 10.0 | 9.5 | 1.0 | 0.0 |
| SECOND MOLAR | 7 | 11.0 | 9.0 | 10.5 | 9.0 | 1.0 | 0.0 |
| THIRD MOLAR | 7.0 | 10.0 | 7.5 | 9.5 | 9.0 | 1.0 | 0.0 |

ROOT FORM ABUTMENT

FIG. 11

TOOTH MESUREMENTS

COLUMN 1

| | Difference in diameter from cervix to crown mesio-distally (mm) | Difference in diameter from cervix to crown bucco-lingually (mm) | Total crown length - mesial curvature (mm) | Total crown length - distal curvature (mm) |
|---|---|---|---|---|
| MAXILLAR | | | | |
| CENTRAL | 1.5 | 1 | 7 | 8 |
| LATERAL | 1.5 | 1 | 6 | 7 |
| CANINE | 2 | 1 | 7.5 | 8.5 |
| FIRST | 2 | 1 | 7.5 | 8.5 |
| SECOND | 2 | 1 | 7.5 | 8.5 |
| FIRST MOLAR | 2 | 1 | 6.5 | 7.5 |
| SECOND MOLAR | 2 | 1 | 6 | 7 |
| THIRD MOLAR | 2 | 0.5 | 5.5 | 6.5 |
| MANDIBULAR | | | | |
| CENTRAL | 1.5 | 0.7 | 6 | 7 |
| LATERAL | 1.5 | 0.7 | 6.5 | 7.5 |
| CANINE | 1.5 | 0.5 | 8.5 | 10 |
| FIRST | 2 | 1 | 7.5 | 8.5 |
| SECOND | 2 | 1 | 7 | 8 |
| FIRST MOLAR | 2 | 0.5 | 6.5 | 7.5 |
| SECOND MOLAR | 2 | 1.5 | 6 | 7 |
| THIRD MOLAR | 2.5 | 0.5 | 6 | 7 |

ROW 1 → points to CENTRAL row; labels 80, 82, 84, 86

FIG. 12

ROOT FORM ABUTMENT

|  | Difference in diameter between 3.75 fixture and tooth diameter at cervix (mm) | Difference in diameter between 4.0 fixture and tooth diameter at cervix (mm) | Difference in diameter between 5.0 fixture and tooth diameter at cervix (mm) |
|---|---|---|---|
| MAXILLAR | | | |
| CENTRAL | 3.25 | 3 | 2 |
| LATERAL | 1.25 | 1 | 0 |
| CANINE | 1.75 | 1.5 | 0.5 |
| FIRST | 1.25 | 1 | 0 |
| SECOND | 1.25 | 1 | 0 |
| FIRST MOLAR | 4.25 | 4 | 3 |
| SECOND MOLAR | 3.25 | 3 | 2 |
| THIRD MOLAR | 2.75 | 2.5 | 1.5 |
| MANDIBULAR | | | -5 |
| CENTRAL | -0.25 | -0.5 | -1.5 |
| LATERAL | 0.25 | 0 | -1 |
| CANINE | 1.75 | 1.5 | 0.5 |
| FIRST | 1.25 | 1 | 0 |
| SECOND | 1.25 | 1 | 0 |
| FIRST MOLAR | 2.75 | 2.5 | 1.5 |
| SECOND MOLAR | 5.25 | 5 | 4 |
| THIRD MOLAR | 3.75 | 3.5 | 2.5 |

FIG. 13

ROOT FORM ABUTMENT

CUSTOMIZED DENTAL ABUTMENT

FIELD OF THE INVENTION

The present invention relates generally to dental implants, and more specifically to the abutments that attaches a bone implanted base to a crown.

BACKGROUND OF THE INVENTION

When restoring a single tooth or multiple teeth with implants, the function of the teeth and the esthetics of the replacement implants are frequently compromised. The patient's primary concern is the improvement of esthetics. The dentist, however, must establish both proper function and acceptable esthetics. Esthetics dictate that the crown (herein defined as the outer, visible part of the replacement) closely resemble the natural tooth structure that is being replaced. That is, the front tooth replacement closely resembles the original tooth, at least when viewed from the front, similarly, replacements for all the other teeth are made to resemble the original teeth.

As presently practiced, the surgical placement of the implanted base or fixture is usually accomplished with few complications. The acceptance of the fixture by the bone is called osseointegration. In the present art these fixtures are narrow cylinders compared to the original tooth. The cylindrical shape is selected probably because the shape is easily produced. The bone and the soft tissue heal and conform to the cylindrical shape of the fixture. But, the crown replicates the original tooth, and is wider and variable in shape compared to the implanted base. Transmucosal abutments, that connect the implant to the crown, have problems caused by these differences in proportions and shapes to which the abutment must comply. In particular, there are significant differences between the presently available abutments and natural teeth. These differences in sizes, orientations, and gingival emerging angles of these available abutments are the cause of discomfort, infection and structural problems.

It is an object of the present invention to provide an abutment which duplicates the natural tooth transmucosal contours, dimensions, and emerging angles. An associated object of the present invention is for the abutment to conform to the natural tooth exposed surface shape.

Another object of the present invention is to provide an abutment that duplicates the natural tooth's inclination and orientation.

It is another object of the present invention to provide an abutment which results in a restoration that is biologically, functionally, and esthetically acceptable.

It is yet another object of the present invention to provide an abutment that functions as the healing abutment and the permanent abutment such that there is no need to replace the healing abutment.

It is yet another object of the present invention to provide a means for duplicating each replacement tooth individually

SUMMARY OF THE INVENTION

The foregoing objects are met in a tooth replacement system and a method for replacing a tooth by an implant, abutment and crown including, measuring the teeth adjacent to the implant site, where the measurements define the size, position, orientation and inclination of the tooth being replaced. The human teeth are composed of several categories with quite different shapes and sizes, the present invention provides a method for determining the type of tooth being replace from the position in the jaw, the type being selected from the group consisting of central, lateral, cuspid, first bicuspid, second bicuspid, first molar, second molar and third molar, implanting a base, contouring the abutment to conform to the gingival emerging size and shape of the natural tooth being replaced, and further contouring the abutment to match the shape contours of the tooth being replaced, attaching the abutment to the base, and attaching to the abutment a crown that matches the shape and contours of the tooth being replaced. In preferred embodiments each specific tooth may be distinguished, and characteristics and measurements determined, where these parameters are used for designing replacement abutments and crowns. The measurements are used to determine the inclination and orientation of a replacement tooth when completed. Inclination is the relative angle of the emerging tooth relative to the gum tissue, and orientation is the rotational position of the tooth compared to the gum and in relation to the neighboring teeth.

The foregoing objects are also met in the physical replacement implant, abutment and crown. The abutment is connected to a bone implanted base, and upon the abutment a crown may be constructed, where the crown duplicates the contours and orientation of the tooth being replaced, the abutment includes a body defining a bottom surface arranged and constructed for connecting to the implanted base, where the body includes an occlusal surface, a facial surface, a buccal surface, a mesial surface and a distal surface, where the occlusal, facial, buccal, mesial, and distal surfaces follow the contours of the natural tooth being replaced.

An advantage of the present invention is the use of one abutment to replace the healing and the permanent abutments of prior art.

Other objects, features and advantages will be apparent from the following detailed description of preferred embodiments thereof taken in conjunction with the accompanying drawings in which:

BRIEF DESCRIPTION OF THE DRAWINGS

FIG. 5A is front (facial) and lateral view of a natural central tooth;

FIG. 5B is front (facial) and lateral view of an implant and abutment replacement corresponding to the tooth of FIG. 5A;

FIG. 5C is top (occlusal) view of the tooth of FIG. 5A;

FIG. 5D is cross section at the cervix of the tooth of FIG. 5A;

FIG. 5E is a top view of the abutment of FIG. 5B;

FIGS. 6A, 6B, 6C, and 6D are views that correspond to FIGS. 5A, 5B, 5C, and 5D, except for a lateral tooth;

FIG. 8 is a group of drawings that correspond to FIGS. 5A, 5B, 5C, and 5D except FIG. 8 applies to the molars;

FIG. 11 is a table of average actual measurements of natural teeth from the data compiled by Wheeler (see reference citation below);

FIG. 12 is a table of values calculated from the values of FIG. 11;

FIG. 13 is a table of values of a replacement tooth compared to natural tooth values.

DETAILED DESCRIPTION OF PREFERRED EMBODIMENTS

Figure 1B:
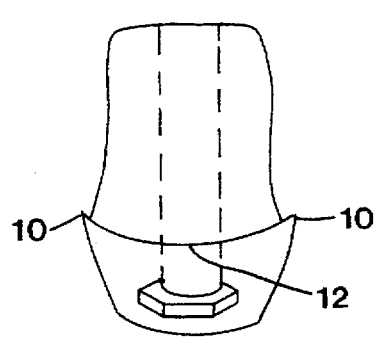
FIG. 1B is a facial view of the abutment of FIG. 1A.
Figure 1A:
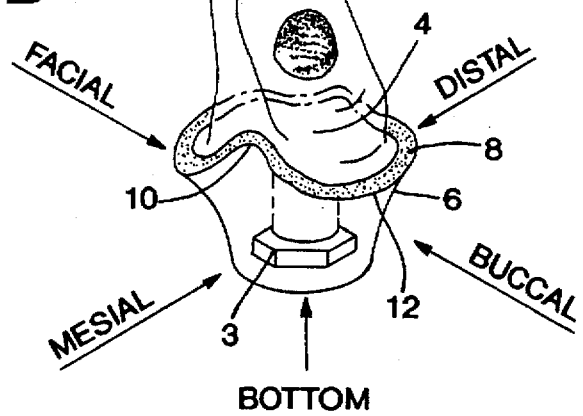
FIG. 1A is a perspective pictorial of an abutment made in accordance with the present invention.

FIG. 1A shows an abutment 2, made in accordance with the present invention for a central tooth. The abutment defines several surfaces generally facing specific directions. The bottom surface is round and configured with a hexagonal incused shape 3 to matingly attach to standard implants. This hexagonal shape provides an anti-rotation feature—a hexagonal shape is well known in the art. There is a through hole 4 running directly through the abutment from the bottom to the top or occlusal surface. The axis of the hole is aligned with the axis of the implant, but differences between these axes to accommodate different inclinations of the replacement tooth and/or orientation may be made to allow the replacement to duplicate the natural tooth as closely as desired.

The directions defined are facial—the surface facing outward; mesial—facing the adjacent central tooth, distal—facing the lateral tooth; buccal—facing inward; and occlusal—facing the opposing upper or lower jaw tooth.

Still referring to FIG. 1A, the transmucosal contour 6 is that part of the abutment that lies partially below and extends to about the visible gingiva (gum) line. This contour 6 ends with a surface 8 that lies at the visible gum line. The surface 8 is contoured to match the gum line that will surround the abutment. The mesial and distal sides form a raised or hill contour 10 while the facial and buccal sides form a depressed or valley contour 12. These shapes conform to the gum line around the natural and the replacement tooth. The final crown will be built on this surface 8. Herein, "replacement tooth" refers to the combination implant, abutment and crown.

FIG. 1B shows the facial side of abutment of FIG. 1A, and FIG. 1B shows the mesial or distal side. The hill 10 and valley 12 contours are clearly shown.

Figure 2:
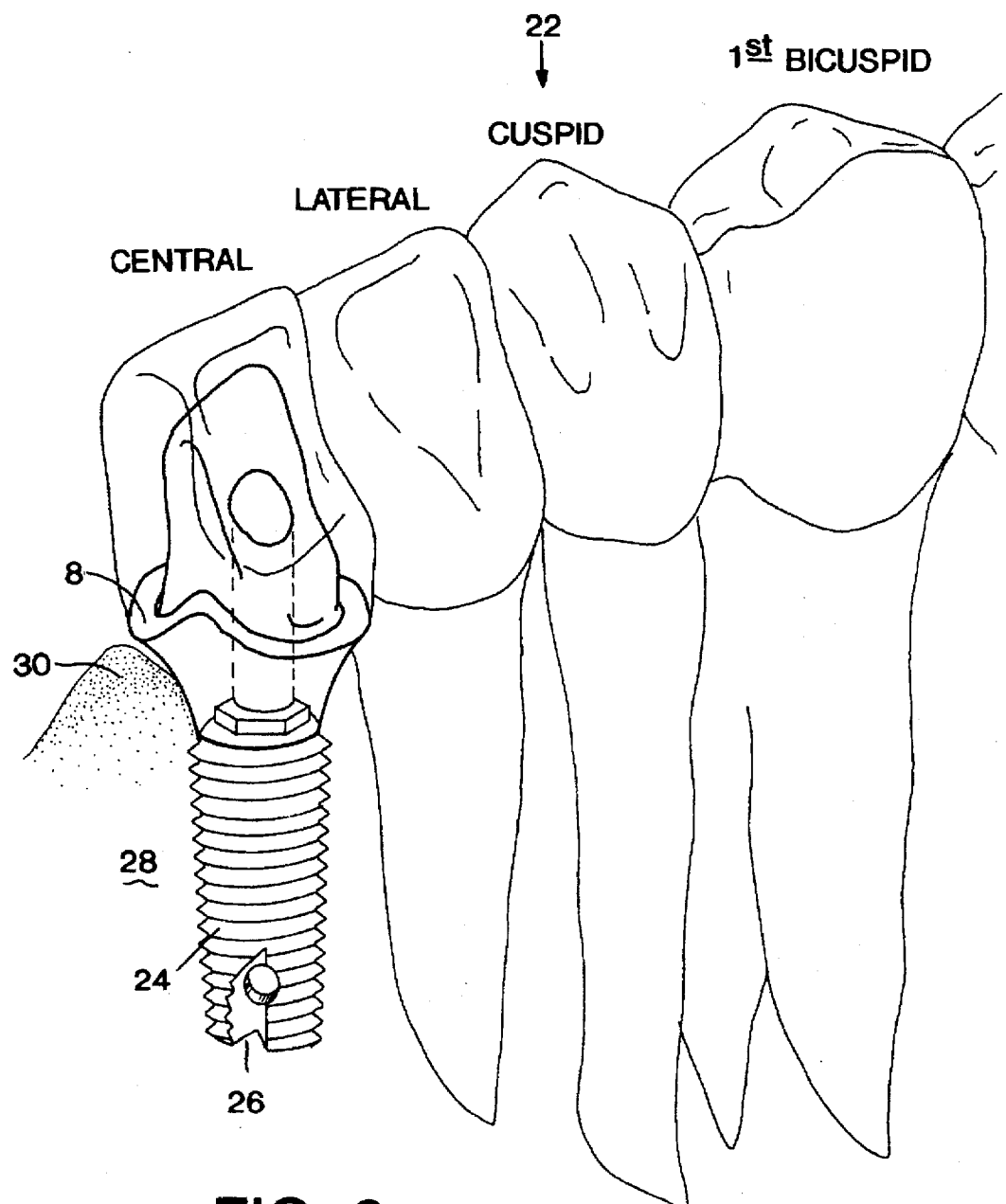
FIG. 2 is a composite view of a completed implanted restored tooth in relation to the surrounding teeth, gum and bone tissue.

FIG. 2 shows the replacement tooth 20 in relation to the adjacent natural teeth 22. The implanted base 24 is shown imbedded into the jaw bone 28. The bottom of the implanted base has an opening 26 that reduces rotation of the implant when the bone grows into this opening. The soft gingival tissue 30 surround the abutment in a natural way.

Figure 3:
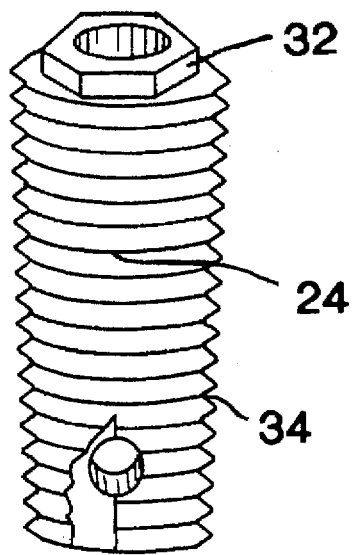
FIG. 3 is a view of a implanted base that is used with the present invention.

FIG. 3 shows the implanted base 24. The top surface of the base is formed into an anti-rotation hex shape 32. This hex surface of the implanted base is about at the bone surface. The abutment has a matching hex incused into the bottom surface and when mated to the implant rotation of the abutment relative to the base is prevented. The rotational position of the implant determines the orientation of the abutment and the crown. The desired orientation of the replacement tooth determine the orientation of the implant so that the hex 32 is configured to match the desired orientation. The base has irregular striations 34 that provide a mechanical attaching feature that helps secure the implant to the bone which grows into these striations. As noted before, there is an opening 26 (of FIG. 2) into which the jaw bone grows to help mechanically secure the implant to the bone and also to prevent rotation of the implant in the jaw bone.

Figure 1C:
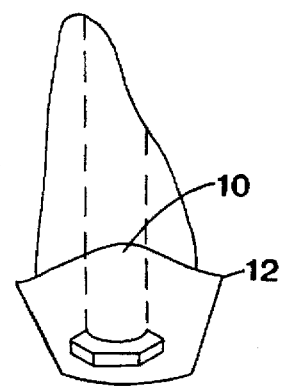
FIG. 1C is a lateral view, mesial or distal, of the abutment of FIG. 1A.
Figure 4:
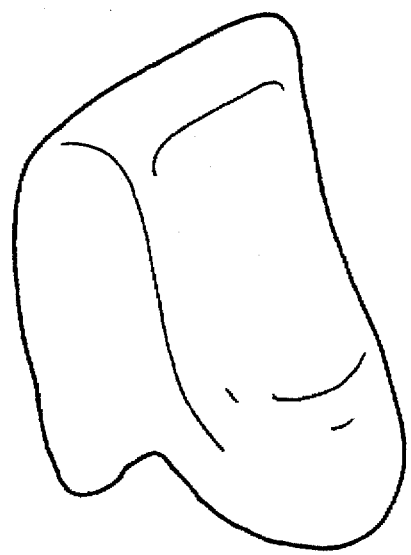
FIG. 4 is a perspective view of a crown that is used with the present invention.

FIG. 4 shows a central tooth crown that would be placed on the abutment of FIGS. 1A, 1B, and 1C. The lateral and top surfaces of the crown are formed to duplicate the natural tooth, and the corresponding surfaces of the present invention abutment have the same shapes.

The preceding preferred embodiment used a central tooth replacement, but any tooth may be replaced using the present invention. Each tooth has a different shape, inclination and orientation. The present invention measures and characterizes each natural tooth such that the replacement is biologically, functionally and esthetically acceptable.

Figure 7:
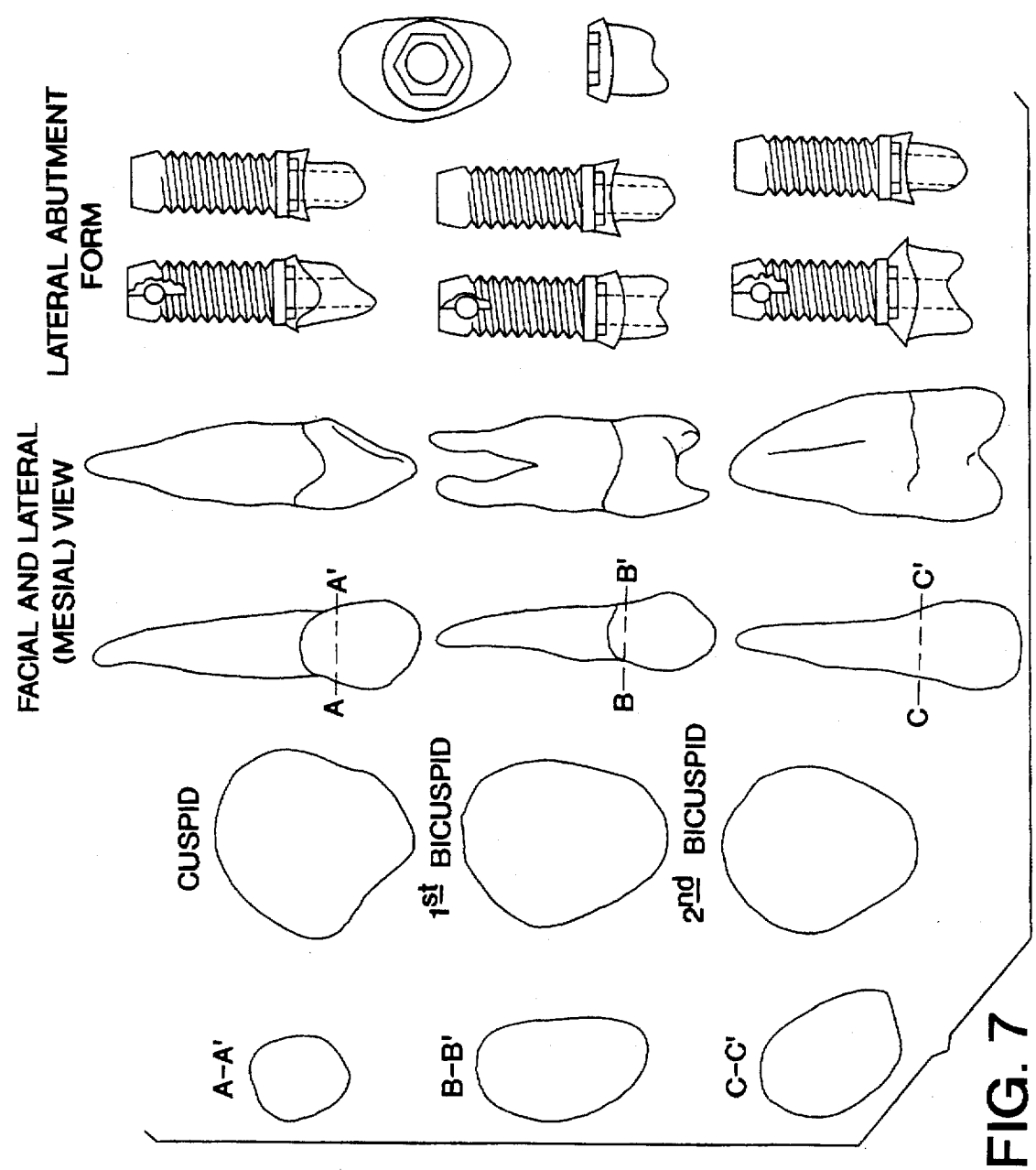
FIG. 7 is a group of drawings that correspond to FIGS. 5A, 5B, 5C, and 5D except for the cuspid, first bicuspid and the first molar.

FIG. 5A, 5B, 5C, and 5D show different perspectives of a tooth replacement made in accordance with the present invention for a central tooth. FIG. 5A is a front and side (lateral) view of a representative central tooth showing the root. On a central tooth the visible outer enamel part 30 is distinguished from the root 33 part. The contour of the line between the outer and the root shows the valley part 36 and the hill part 34 (the directions are reversed from FIG. 1A since the tooth is shown reversed from that of FIG. 1A) where the gum line meets the tooth surface. The hill/valley contour is matched in the present invention abutment. The abutment that replaces the tooth of FIG. 5A is shown in FIG. 5B. The hill 10 of the abutment matches the natural tooth hill 34 and the valley 12 of the abutment matches the valley 36 of the natural tooth. The implanted base 24 approximates the natural tooth root. In addition, the present invention provides that the surfaces 30' of the abutment match the shapes of the natural tooth. Of course, the abutment outer surface onto which the crown is placed is smaller than the outer surface of the crown, but the general, or even the detailed surface shapes or contours correspond to each other. Within the present invention, the shapes of the natural ,and abutment may be made to closely or roughly equal each other as a specific application may require. FIG. 5C shows the central tooth from an opposite tooth, and FIG. 5D shows the basic triangular cross section shape at the cervix (section A—A') of a central tooth. FIG. 5E is the occlusal view looking down through the abutment to the implant. The general shape of the abutment of FIG. 5E and FIG. 5D match each other. FIG. 6A, 6b, 6C, and 6D show views of a lateral tooth corresponding to those preceding (FIGS. 5A, B, C, D) for a central tooth. FIG. 7 shows the corresponding views for the cuspid, first bicuspid, and second bicuspid. Of note, is the shape of these teeth taken at the cervix of the tooth, shown in FIG. 7 as the sections taken at A—A', B—B', and C—C' (drawings not to scale) where the shapes are ovoid. FIG. 8 shows the corresponding views of a molar where the cervix shape shown in section A—A' is a squared shape for the lower molars and a rhomboid shape for the upper molars.

Figure 9:
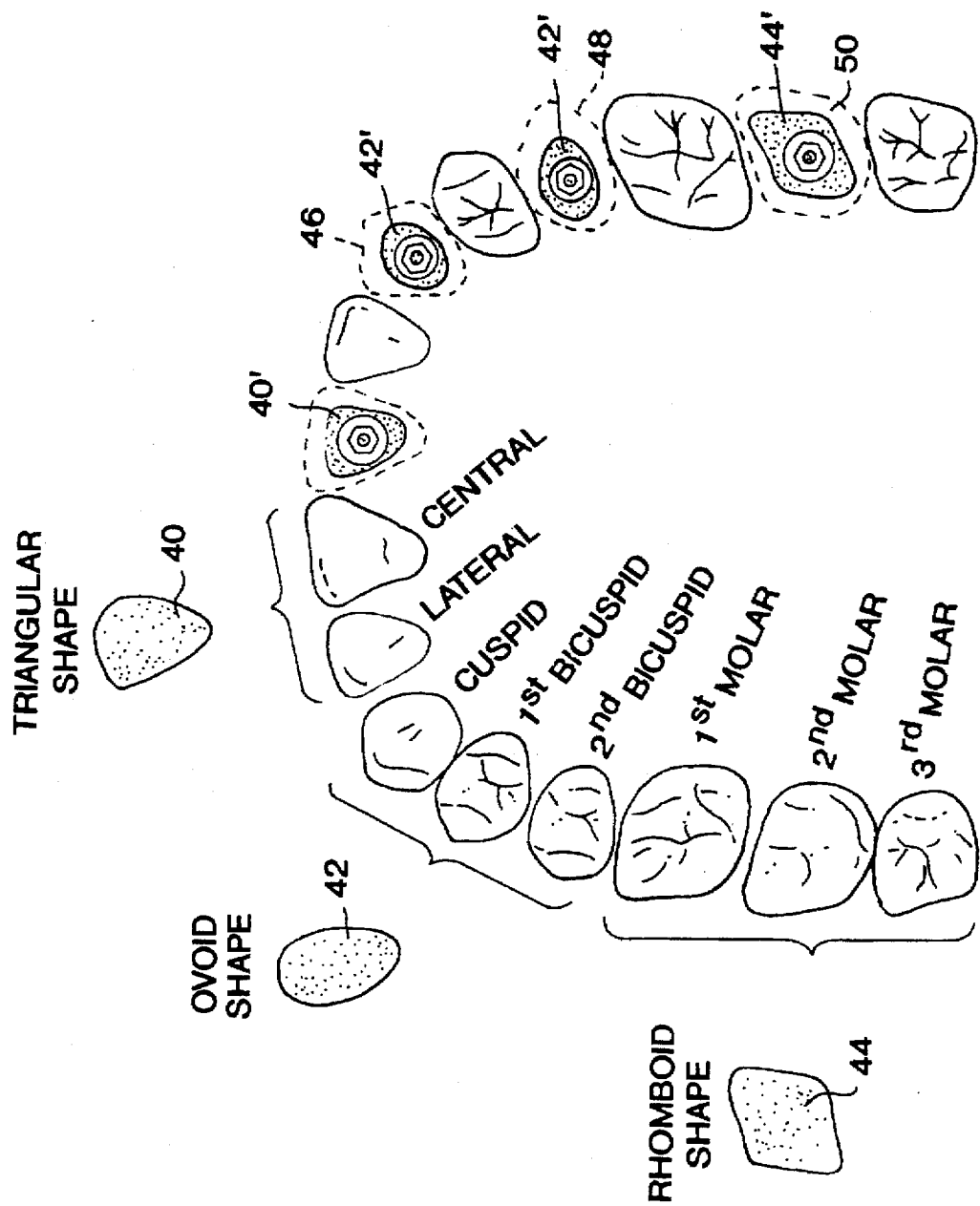
FIG. 9 is a occlusal view of a complete set of teeth showing the relative positions of each type.

FIG. 9 is a complete occlusal view of the teeth of the upper jaw (maxillar). The central and lateral teeth share a triangular tooth shape 40 at the cervix or gum line, the cuspid and bicuspids share an ovoid shape 42, and the molars a rhomboidal shape 44. The cutaways show the abutments 40', 42' showing a different orientation between the cuspid 46 and the second bicuspid 48, and the second molar 50.

The implant must be positioned in the jaw bone at the proper relative position and at the proper angle, where the relative positions are measured from all other teeth, and the angles are measured from all directions with respect to the angles of adjacent teeth and/or the face construction. With such measurements as a guide the implant, abutment and crown will closely approximate the actual tooth being replaced.

Figure 10:
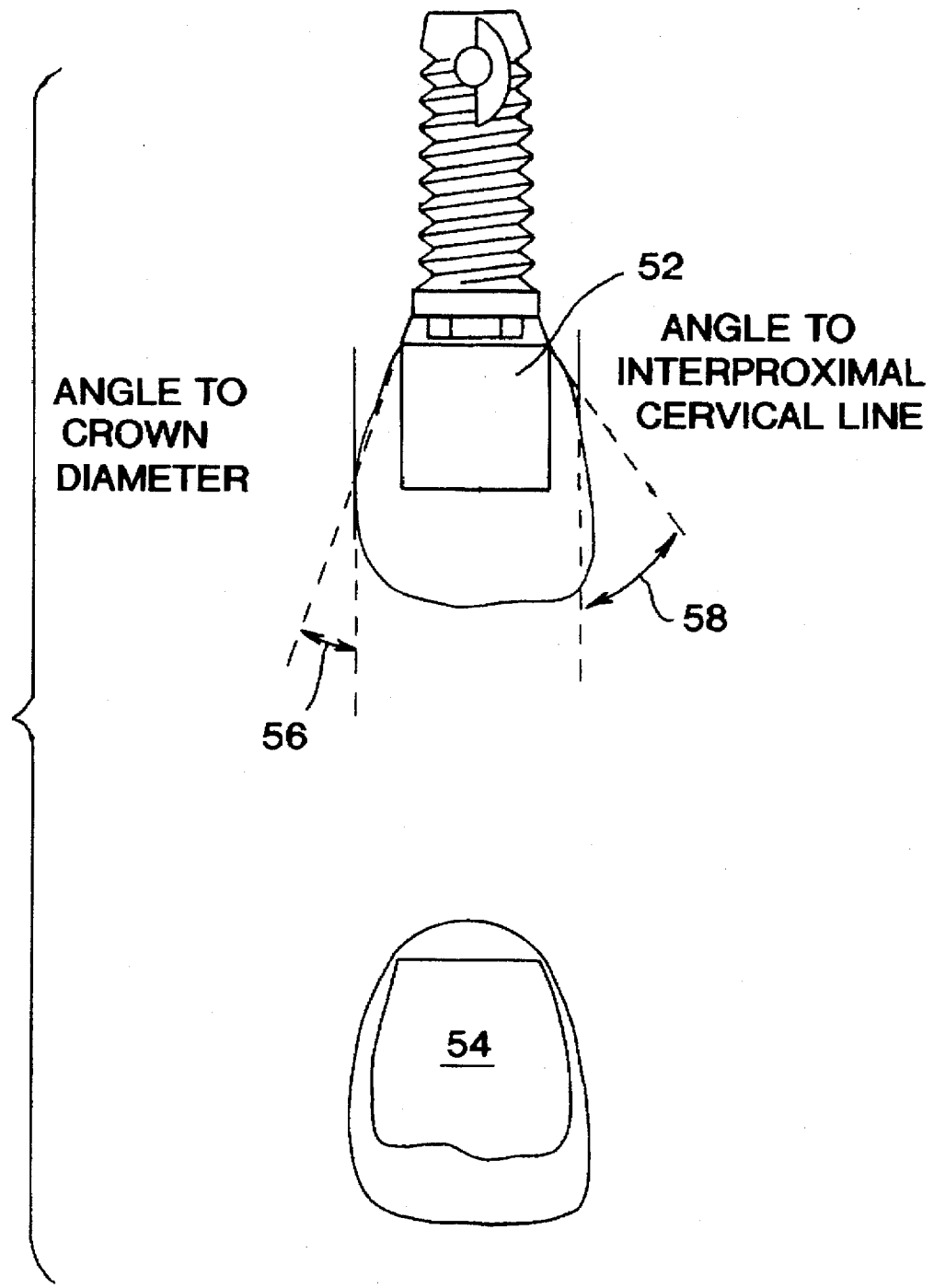
FIG. 10 is a comparison drawing of a natural and a replacement tooth
Figure 14:
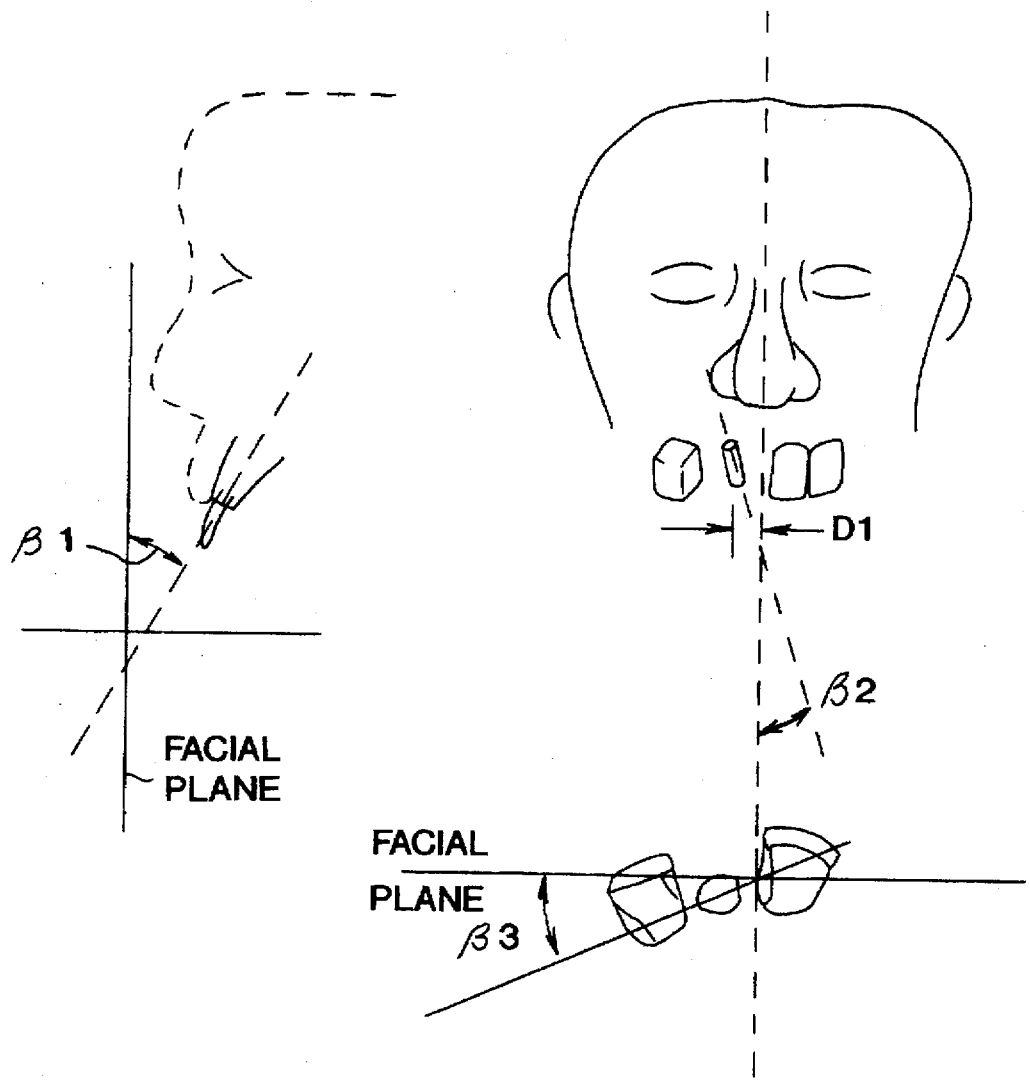
FIG. 14 shows other views of teeth showing some other dimensions.

FIG. 10 show a side by side comparison of a now available abutment 52 and an abutment 54 made in accordance with the present invention. The conformity of the inventive abutment to the angles of the natural tooth are directly evident from the drawing. The angle 56 of a line from the cervical edge to the crown diameter compared to a vertical line is matched with the inventive abutment compared to the available abutments. The angle of the inventive abutment contour at the cervical line is also matched by the inventive abutment compared to the available abutments.

FIGS. 11, 12 are tables of data from "*DENTAL ANATOMY, PHYSIOLOGY AND OCCLUSION*", by Russell C. Wheeler, first published by "W. B. Saunders Company", 1940 (hereinafter "Wheeler"). These data show the measurement required to fabricate and position abutments for all the different teeth.

FIGS. 11 and 12 show relative measurements of teeth taken at various locations. These measurements are average measurements for natural teeth as described in Wheeler. These measurements are the base data used for software developed as described herein. Similar measurements may be taken by the dentist by several means including a stent, from molds of the teeth, any optical device available, or any other measuring instrument available—in short any available process and/or instrumentation may be used to take these measurements. The top eight rows 60 represent measurements taken on the upper jaw teeth, and the lower eight rows are for the lower jaw teeth. The dentist may use the patient's actual measurements to modify or personalize the computer program that will generate the abutment as described herein. It is well understood, within the programming art, how to program a computer to perform the specific individual tasks to control and guide the constructing of an abutment in accordance with the present invention.

The first column 64 is the length of the crown from the cemented enamel junction (CES) to the occlusal tip of the crown taken directly through the axis of the tooth, column 66 is the width of the crown between adjacent teeth, column 68 the width at the CES, column 70 is the front to back width of the crown, column 72 is the front to back width of the crown at the CES, and columns 74 and 76 record the spreading of the tooth from the cervix (CES) to the widest part of the crown when viewing the tooth from the outer facial surface. Column 74 for the side of the mesial side of the tooth and column 76 for the distal side of the tooth.

FIG. 12 show the diameter differences taken from FIG. 11 and the total lengths, also taken from FIG. 11. For example, the value 1.5 mm in row 1, column 1 of FIG. 12 is calculated by subtracting the 7.0 mm of row 60', column 68 from the 8.5 mm of row 60', column 66. In a similar fashion the values of FIG. 12 columns 2,3 and 4 are calculated. Location 82 is found by subtracting the values found in FIG. 11, row 60', column 72 from column 70; location 84 is found by subtracting the values found in FIG. 11, row 60', column 74 from column 64; and the value 86 is found by subtracting the values found in FIG. 11, row 60', column 76 from column 64. In a similar way all the other measurements of FIG. 12 may be calculated.

Various sizes and measurements of abutments now being produced by manufacturers are of a cylindrical form and are well known in the art. These cylindrical forms are contrasted to the present invention. The standard diameters are 3.75 mm, 4 mm, and the 5 mm. FIG. 13 shows the differences between the average size measurements of Wheeler and the sizes of the standard cylindrical fixtures. In FIG. 13, column 96 lists several different teeth and the columns 98, 100, and 102 list the differences between the actual average measurements of natural teeth and the presently available standard cylindrical abutments. The differences are taken at the cervix which, as previously described, is at or near the gum line. These differences illustrate the need for an abutment which more closely conforms to the natural tooth measurements.

What is claimed is:

1. A method for replacing a tooth, said tooth having shade and contoured surfaces, by an implant, abutment and crown comprising the steps of:

measuring the teeth adjacent to the implant site, where said measurements define the size, position, orientation and inclination of the tooth being replaced, determining the type of tooth being replaced from the position in the jaw, said type being selected from the group consisting of central, lateral, cuspid, first bicuspid, second bicuspid, first molar, second molar and third molar, implanting a base, contouring an abutment to conform to the gingival emerging size and shape of the tooth being replaced, and further contouring the abutment to follow said respective shape and contours of the tooth being replaced, attaching the abutment to the base, and attaching a crown to the abutment, where the crown matches the shape and contours of the tooth being replaced.

2. A method as defined in claim 1 wherein the step of measuring comprises the steps of:

measuring the relative positions of the adjacent and other teeth to the position of the implant, abutment and crown, measuring the angles of the adjacent teeth and the angle of the face construction relative to the angles of the implant, abutment and crown, inputting said measurements into a computer, programming the computer to determine the size, orientation, inclination and shape of the tooth being replaced from said measurements, outputting from the computer information to guide and control the contouring of the abutment surfaces and the abutment dimensions.

3. A method as defined in claim 2 further comprising the steps of:

under the guidance of the computer, fabricating an abutment to match the gingival emerging profile of the tooth being replaced, and fabricating a crown to match the shape, size and inclination and orientation of the tooth being replaced.

* * * * *